US00PP16462P2

(12) United States Plant Patent
Bradford

(10) Patent No.: US PP16,462 P2
(45) Date of Patent: Apr. 18, 2006

(54) PEACH TREE NAMED 'CANDY PRINCESS'

(50) Latin Name: *Prunus persica*
Varietal Denomination: Candy Princess

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 107 days.

(21) Appl. No.: 11/029,692

(22) Filed: Jan. 6, 2005

(51) Int. Cl.
*A01H 5/00* (2006.01)

(52) U.S. Cl. ..... Plt./198
(58) Field of Classification Search ..... Plt./198
See application file for complete search history.

(56) References Cited

U.S. PATENT DOCUMENTS

PP6,045 P * 10/1987 Jost ..... Plt./198
PP7,507 P 4/1991 Bradford
PP8,597 P * 2/1994 Viscarra ..... Plt./198
PP9,102 P * 4/1995 Avila ..... Plt./198
PP14,677 P2 4/2004 Bradford

* cited by examiner

*Primary Examiner*—Anne Marie Grunberg
*Assistant Examiner*—W. C. Haas

(57) ABSTRACT

The present invention relates to a peach tree, *Prunus persica,* and more particularly to a new and distinct variety characterized by a medium size, vigorous, hardy, self-fertile, productive and regular bearing tree. The fruit matures under the ecological conditions described approximately the third week in July, with first picking on Jul. 20, 2003. The fruit is uniformly large in size, sub-acid and sweet in flavor, globose in shape, freestone in type, firm in texture, yellow with some red streaking in flesh color, and mostly red in skin color. The variety was developed as a first generation cross using 'Spring Bright' (U.S. Plant Pat. No. 7,507) yellow flesh nectarine as the selected seed parent and an unnamed peach as the selected pollen parent.

1 Drawing Sheet

Latin name: *Prunus persica.*
Varietal denomination: 'Candy Princess'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'Candy Princess'. The present variety was hybridized by me in 1996, grown as a seedling on its own root in my greenhouse, and transplanted to a cultivated area of my experimental orchard at Bradford Farms near Le Grand, Calif. in Merced County (San Joaquin Valley).

The variety was developed as a first generation cross using 'Spring Bright' (U.S. Plant Pat. No. 7,507) yellow flesh nectarine as the selected seed parent and an unnamed peach (unpatented) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Spring Bright' (U.S. Plant Pat. No. 7,507) nectarine, by producing fruit that is globose in shape, firm and crisp in texture, mostly red in skin color, and yellow in flesh color, but is very distinguished therefrom and an improvement thereon by producing fruit that is freestone instead of clingstone, that is sub-acid instead of acid in flavor, that matures about four weeks later, and that is peach instead of nectarine.

The present variety is most similar to 'Spring Candy' (U.S. Plant Pat. No. 14,677) peach by sharing the same parentage and by producing peaches that are freestone in type, nearly full red in skin color, yellow with some red streaking in flesh color, firm in texture, and sub-acid in flavor, but is distinguished therefrom by producing peaches that are larger in size and that mature about three weeks later.

SUMMARY OF VARIETY

In summary, the present variety is characterized by a medium size, vigorous, hardy, self-fertile, productive and regular bearing tree. The fruit matures under the ecological conditions described approximately the third week in July, with first picking on Jul. 20, 2003. The fruit is uniformly large in size, sub-acid and sweet in flavor, globose in shape, freestone in type, firm in texture, yellow with some red streaking in flesh color, and mostly red in skin color.

DRAWING

The accompanying photograph consists of four whole fruits positioned to display the characteristics of the skin color and form, one fruit divided along the suture plane to reveal the flesh and stone, typical leaves, and three insets depicting buds, flowers, and various flower parts.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif. The fruit description was developed at the state of eating ripe on Jul. 28, 2003, on the original tree during its seventh growing season. The flower and bud descriptions were developed the following blooming season. All major color code designations are by reference to the Inter-Society Color Council, National Bureau of Standards. Common color names are also used occasionally.

TREE

Size: Medium, reaching a height of 12' [3.66 m.] and a spread of 9' [2.74 m.] after seven growing seasons utilizing typical dormant pruning.

Vigor: Medium, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Original tree was trained by pruning to be vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Trunk:

*Size.*—Medium, with a maximum diameter of 4" [102 mm.] after the seventh growing season.

*Texture.*—Shaggy.

*Bark color.*—Dark grayish brown [62. d.gy.Br].

*Lenticels.*—Approximate Number Per Square Inch: 10. Color: Light orange yellow [70. l.OY]. Size: ⅛" [3.2 mm.] to 7/16" [11.1 mm.]. Shape: Eye-shaped to elongated.

Branches:

*Size.*—Diameter of main scaffold is 2½" [64 mm.] measured 12" above the crotch, diameter of limb is 1½" [38 mm.] measured 12" above the first fork, typical of *Prunus persica,* and dependent upon cultural practices and climatic conditions.

*Texture.*—Smooth on 1st year wood, increasing roughness with age.

*Color.*—1st Year Wood Topside: Light grayish red [18. l.gy.R]. 1st Year Wood Underside: Very yellow green [115. v.YG]. Older Wood: Deep yellowish brown [75. deep yBr].

*Lenticels.*—Number Per Square Inch: More than 80 on second year wood. Color: Pale orange yellow [73. p.OY]. Typical size: 1/32" [0.8 mm.] to ⅛" [3.2 mm.]. Shape: Eye-shaped to elongated.

Leaves:

*Size.*—Large. Average Length: 5¾" [146 mm.]. Average width: 1⅝" [41 mm.].

*Arrangement.*—Alternate.

*Thickness.*—Medium.

*Form.*—Elliptical.

*Apex.*—Acuminate.

*Base.*—Acute to rounded.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Light yellow green [119. l.YG].

*Stipules.*—Number: Up to 6 per growing tip. Average Length: 5/16" [7.9 mm.]. Color: Very yellow green [115. v.YG] when young becoming Dark yellowish brown [78. d.yBr] with age.

*Glands.*—Number: 2 to 4. Position: Usually opposite, first two on petiole and the rest on base of leaf blade. Size: Medium. Form: Reniform. Color: Brilliant yellow green [116. brill.YG] becoming Grayish brown [61. gy.Br] in the center with age.

*Leaf buds.*—Conic.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepals and petal locations alternately positioned.

*Type.*—Showy, very large.

*Average flower diameter.*—2" [50.8 mm.].

*Number of petals.*—Usually five, with a small percentage of double blossoms observed.

*Petal shape.*—Circular.

*Petal margin.*—Somewhat wavy.

*Average petal diameter.*—13/16" [20.6 mm.].

*Average petal length.*—⅞" [22.2 mm.].

*Petal apex.*—Rounded.

*Petal base.*—Rounded to slightly truncate.

*Petal color.*—Pale pink [7. p.Pk] toward the apex smoothly blending into Strong purplish pink [247. s.pPk] toward the base.

*Anther color.*—Dark red [116 d.R] surrounding a Light orange yellow [70. l.OY] center.

*Stigma color.*—Light greenish yellow [101. l.gY].

*Sepal color.*—Dark purplish red [259. d.pR].

*Sepal length.*—5/16" [7.9 mm.].

*Sepal width.*—¼" [6.4 mm.].

*Average pistil length.*—¾" [19.1 mm.].

*Average stamen length.*—⅝" [15.9 mm.].

*Fragrance.*—Moderate.

*Blooming period.*—Early to medium compared with other varieties.

*Onset of bloom.*—One percent on Feb. 25, 2003.

*Date of full bloom.*—Mar. 5, 2003.

*Duration of bloom.*—One to two weeks, dependent on ambient temperature.

*Number per cluster.*—1 to 3 with single flowers most common.

FRUIT

Maturity when described: Eating ripe, Jul. 28, 2003.

Date of first picking: Jul. 20, 2003.

Date of last picking: Aug. 1, 2003.

Size: Uniform, large.
*Average diameter axially.*—2⅞" [73.0 mm.].
*Average diameter across suture plane.*—3⅛" [79.4 mm.].
*Typical weight.*—10.7 ounces [303 grams].
Form: Uniform, mostly symmetrical, globose to slightly oblate.
*Longitudinal section form.*—Elliptical.
*Transverse section through diameter.*—Circular.
Suture: A shallow groove from the base to slightly beyond the apex with a marked depression just beyond the pistil point, sharper near the base and apex.
Ventral surface: Rounded, lipped toward the apex on both sides.
Lips: Slightly unequal.
Cavity: Flaring, elongated in the suture plane, suture showing on both sides, with Brilliant yellow [83. brill.Y] stem markings typical.
*Depth.*—½" [12.7 mm.].
*Breadth.*—1¼" [31.8 mm.].
Base: Somewhat truncate.
Apex: Rounded to truncate.
Pistil point: Usually apical, negligible in length, depressed within the suture.
Stem: Medium.
*Average length.*—⅜" [9.5 mm.].
*Average width.*—3/16" [4.8 mm.].
Skin:
*Thickness.*—Medium.
*Texture.*—Pubescent.
*Tenacity.*—Tenacious to flesh.
*Astringency.*—Nonastringent.
*Tendency to crack.*—None observed.
*Color.*—Dark red [16. d.R] smoothly blending into a Strong reddish orange [35. s.rO] background with a few Brilliant yellow [83. brill.Y] areas where sun protected.
Down: Scant, short in length, does not roll up when rubbed.
Flesh:
*Color.*—Very Yellow [82. v.Y] with Deep red [13. deep R] streaking from the stone outward.
*Surface of pit cavity.*—Freestone with Very deep red [14. v.deep R] fibers.
*Amygdalin.*—Scarce.
*Juice.*—Abundant, rich.
*Texture.*—Firm, crisp and melting.
*Fibers.*—Abundant, fine and tender.
*Ripens.*—Slightly earliest at the apex.
*Flavor.*—Sweet and sub-acid, typically 16 brix.
*Aroma.*—Very slight.
*Eating quality.*—Very good.

STONE

Type: Fragrance.
Form: Oval.
Hilum: Narrow, oblong.
Base: Slightly oblique.
Apex: Acute, with an average base angle of 80 degrees and a tip length of 3/32" [2.4 mm.].
Sides: Equal.
Surface: Irregularly furrowed near the apex and pitted toward the base.
Ridges: Jagged toward the base.
External color: Dark brown [59. d.Br].
Average pit wall thickness: 5/16" [7.9 mm.].
Average width: 1⅛" [28.6 mm.].
Average length: 1⅜" [34.9 mm.].
Average breadth: 13/16" [20.6 mm.].
Tendency to split: Slight.
Kernel:
*Form.*—Oval.
*Skin color.*—Strong yellowish brown [74. s.yBr] when dry.
*Pellicle color.*—Deep yellowish brown [75. deep yBr].
*Vein color.*—Deep yellowish brown [75. deep yBr].
*Taste.*—Bitter.
*Viable.*—Yes.
*Average width.*—9/16" [14.3 mm.].
*Average length.*—¾" [19.1 mm.].
*Amygdalin.*—Abundant.

USE

Market: Fresh market and long distance shipping.
Keeping quality: Good. Fruit quality observed to remain in good condition in after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Spring Candy' (U.S. Plant Pat. No. 14,677) peach by sharing the same parentage and by producing peaches that are freestone in type, nearly full red in skin color, yellow with some red streaking in flesh color, firm in texture, and a sweet sub-acid in flavor, but is distinguished therefrom by producing peaches that are larger in size and that mature about three weeks later.

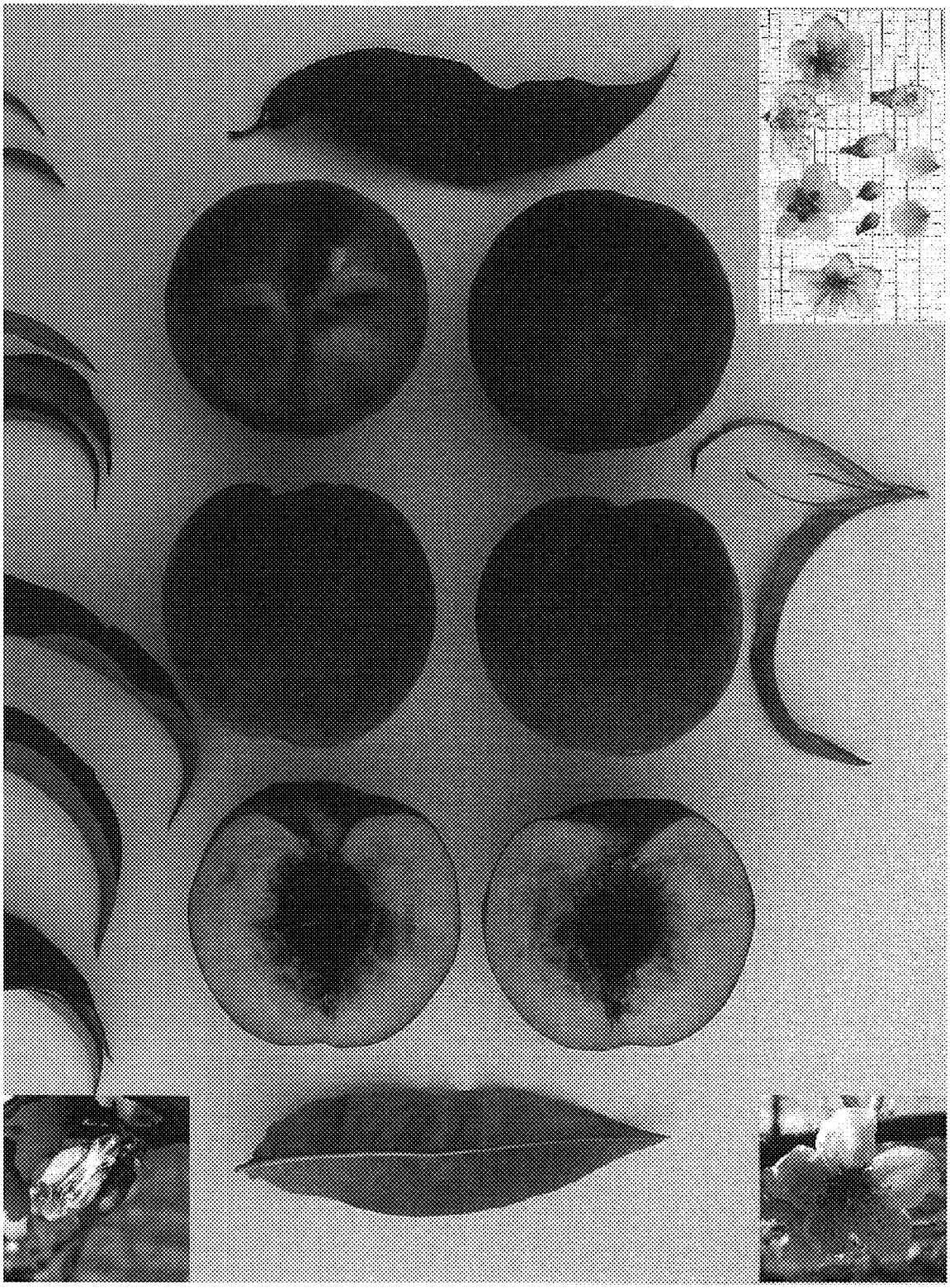

* * * * *